United States Patent [19]

McEwen

[11] Patent Number: 5,181,522

[45] Date of Patent: * Jan. 26, 1993

[54] TOURNIQUET FOR SENSING AND REGULATION OF APPLIED PRESSURE

[75] Inventor: James A. McEwen, Richmond, Canada

[73] Assignee: Abatis Medical Technologies Limited, Dublin, Ireland

[*] Notice: The portion of the term of this patent subsequent to Sep. 17, 2008 has been disclaimed.

[21] Appl. No.: 759,514

[22] Filed: Sep. 13, 1991

Related U.S. Application Data

[63] Continuation-in-part of Ser. No. 388,699, Jul. 13, 1989, Pat. No. 5,048,536, which is a continuation-in-part of Ser. No. 33,770, Apr. 3, 1987, Pat. No. 4,869,265.

[51] Int. Cl.$^5$ .............................................. A61B 5/00
[52] U.S. Cl. .................................... 128/748; 128/774; 606/203
[58] Field of Search ................ 128/686, 748, 774–782; 606/201–203; 200/83 N, 83 Y, 81.4, 211, 212, 214

[56] References Cited

U.S. PATENT DOCUMENTS

| 3,095,873 | 7/1963 | Edmunds | 128/205 |
| 4,469,099 | 9/1984 | McEwen | 128/327 |
| 4,479,494 | 10/1984 | McEwen | 128/327 |
| 4,605,010 | 8/1986 | McEwen | 128/686 |
| 4,770,175 | 9/1988 | McEwen | 128/327 |

OTHER PUBLICATIONS

J. A. McEwen and R. W. McGraw, "An adaptive tourniquet for improved safety in surgery," IEEE Trans. Bio-Med Eng., vol. BME29, 1982, pp. 122–128.

J. A. McEwen and G. F. Auchinleck, "Advances in surgical tourniquets," J.A.O.R.N, vol. 36, 1982, pp. 889–896.

J. A. Shaw and D. G. Murray, "The relationship between tourniquet pressure and . . ." J. Bone & Joint Surg., vol 64-A, 1982 pp. 1148-1152.

A. C. McLaren and C. H. Rorabeck, "The pressure distribution under tourniquets," J. Bone & Joint Surg., 67A, 1985, pp. 433-438.

R. J. Newman and A. Muirhead, "A safe & effective low press. tourniquet." J. Bone & Joint Surg., 68B, 1986, pp. 625-628.

J. A. Shaw et al., "Guidelines for the use of digital tourniquets . . ." J. Bone & Joint Surg., 67A, 1985, pp. 1086-1090.

S. E. Grice et al., "Intravenous regional anesthesia: evaluation and prevention of leakage . . ." Anesthesiology, 65, pp. 316-320, 1986.

Primary Examiner—Max Hindenburg
Attorney, Agent, or Firm—Klarquist Sparkman Campbell Leigh & Whinston

[57] ABSTRACT

A tourniquet system comprising: an inflatable occlusive band for encircling a limb of a subject and for inflating to apply pressure to the encircled limb to occlude blood flow into the limb distal to the band, wherein an inner surface of the band faces the limb; inflation pressure regulation means responsive to a variable inflation pressure regulation signal for regulating the pressure to which the occlusive band is inflated and for producing an inflation pressure signal representative of the pressure to which the band is inflated; applied pressure sensing means located at a predetermined location fixed relative to the band for producing an applied pressure signal representative of the pressure applied by the inflated band to the limb in a direction normal to inner surface of the band at the predetermined location; and pressure-regulating means responsive to the applied pressure signal for producing an inflation pressure regulation signal to maintain the pressure applied by the inflated band to the limb at the predetermined location near a predetermined reference pressure. The tourniquet system may include pressure comparison means for comparing the difference between the pressures represented by the inflation pressure signal and the applied pressure signal and for and generating an alarm signal if the difference exceeds a preassigned limit.

16 Claims, 5 Drawing Sheets

TOURNIQUET FOR SENSING AND REGULATION OF APPLIED PRESSURE

REFERENCE TO RELATED APPLICATION

This is a continuation-in-part of U.S. patent application Ser. No. 07/388,699, filed Jul. 13, 1989, U.S. Pat. No. 5,048,. which was a continuation-in-part of U.S. patent application Ser. No. 07/033,770, filed Apr. 3, 1987, U.S. Pat. No. 4,869,..

FIELD OF THE INVENTION

This invention pertains to medical devices which apply, estimate and control pressure on a tissue, organ or limb of a living body near predetermined locations relative to the devices. The invention particularly pertains to a tourniquet useful in surgery for controlling and occluding blood flow into a portion of a limb, comprising: an inflatable occlusive band for encircling a limb of a subject and for inflating to apply pressure to the encircled limb wherein an inner surface of the band faces the limb; inflation pressure regulation means responsive to a variable inflation pressure signal for regulating the pressure to which the band is inflated and for producing an inflation pressure signal representative of the pressure to which the band is inflated; applied pressure sensing means located at a predetermined location fixed relative to the band for producing an applied pressure signal representative indication of the pressure applied by the inflated band to the limb near the predetermined location; and pressure-regulating means responsive to the applied pressure signal for producing an inflation pressure regulation signal to maintain the pressure applied by the inflated band to the limb at the predetermined location near a predetermined reference pressure.

BACKGROUND OF THE INVENTION

Surgical tourniquet systems are widely used to facilitate surgical procedures on portions of arms or legs of patients by occluding blood flow into those limb portions for periods ranging from a few minutes to several hours. During operations performed under intravenous regional anesthesia, the surgical tourniquet system serves an additional role of preventing local anesthetic agent introduced into the veins of the operative limb distal to the occlusion from flowing out of the limb into the circulatory system.

A surgical tourniquet system at present typically includes a cuff with an inflatable bladder for encircling the limb and for applying pressure to the encircled limb, pressure regulating means intended for maintaining the pressure within the cuff bladder near a desired pressure, and means for setting the desired pressure, either at a constant level or varying in response to a changing parameter such as systolic, mean or diastolic blood pressure.

Operative and post-operative complications associated with the use of all tourniquet systems described in the prior art are related almost entirely to the pressure applied by the cuff to the limb and hence to the underlying vessels and tissues. As described in the cited prior art, application of insufficient pressure to the limb by the cuff will permit blood to flow into the field of surgical dissection, thereby complicating the procedure and potentially extending the duration of the operation significantly. This is a particularly hazardous situation for operations performed under intravenous regional anesthesia (IVRA). Application of insufficient pressure to the limb by the cuff during administration of IVRA may allow anesthetic agent injected into the veins of the limb to escape into the circulatory system in high concentration, which can cause serious adverse reactions such as cardiovascular collapse, respiratory depression, epileptic seizures or even death.

The results of tests performed on animals, cadavers and to some extent humans, as described in the cited prior art, clearly indicate that high pressures and high pressure gradients applied to the limb by the cuff are associated with higher probabilities of underlying nerve injury, whereas lower applied pressures and lower applied pressure gradients are associated with lower probabilities of nerve injury. These recognized hazards and experimental findings would appear to have important implications for surgical tourniquet systems, but surprisingly no tourniquet system known to the applicant in the prior art regulates the gas pressure within the inflatable bladder of the cuff and simultaneously estimates the pressure actually applied by the cuff to the limb near one or more predetermined locations relative to the cuff.

Recently, research and clinical investigations were completed using a tourniquet cuff incorporating a novel biomedical pressure transducer disclosed by McEwen in U.S. Pat. No. 4,869,265 issued Sep. 26, 1989. The clinical investigations performed using the novel biomedical transducer have revealed many significant discrepancies between the pressure maintained in the inflatable bladder of the pneumatic tourniquet cuff and the pressure actually applied by the cuff to the encircled limb. Normal variations in technique used to apply the cuff to the limb were found to vary the maximum pressure actually applied to the limb by 50 percent or more in comparison to the bladder pressure of the cuff, which was regulated within $+/-1\%$ of a preassigned reference pressure by the tourniquet system. In light of the hazards described previously, such a variation is clearly undesirable and in many clinical situations, such as in the use of intravenous regional anesthesia, such a discrepancy can be life-threatening.

Further tests with a tourniquet cuff including the above-referenced biomedical pressure transducer have revealed significant pressure variations in the pressure applied to a limb in a circumferential direction, particularly in the region where the cuff overlaps itself as it encircles the limb. As described above, these pressure variations can result in serious surgical complications.

No tourniquet system in the prior art known to the applicant accurately estimates the level of pressure actually applied to the limb by an inflatable cuff of such a system near a predetermined location, and also employs that estimate of the applied pressure to control the pressure regulator of the tourniquet system so that the pressure applied by the cuff to the limb is maintained near a predetermined reference pressure. Moreover, the applicant is unaware of any surgical tourniquet system known in the prior art which compares the difference between the level of pressure actually applied to the limb by the cuff and the pressure in the inflated bladder of the cuff for the purpose of generating an alarm if a significant difference exists. The applicant is also unaware of any surgical tourniquet system known in the prior art which produces an indication of the applied pressure to the clinical user of the tourniquet system. In addition to mitigating the aforementioned operative and post-operative complications, features such as these would be useful for detecting and indicating cuff misapplication, calibration error in one or more pressure sensors, or pressure sensor failure.

An object of the present invention is to provide a tourniquet system comprising an inflatable occlusive cuff for encircling and applying an occlusive pressure to a limb of a subject, means for controlling the pressure to which the cuff is inflated, means for sensing the pressure applied by the inflated cuff to the limb in a direction normal to the inner surface of the cuff at a predetermined location, and including pressure comparison means for producing an alarm if the difference between the pressure to which the cuff of the tourniquet system is inflated and the pressure applied by the inflated cuff to the limb exceeds a preassigned safety limit.

Another object of the present invention is to provide a tourniquet system comprising an inflatable occlusive cuff for encircling and applying an occlusive pressure to a limb of a subject, means for sensing the pressure applied by the inflated cuff to the limb in a direction normal to the inner surface of the cuff at a predetermined location, and means responsive to the pressure applied by the inflated cuff to the limb for regulating the pressure to which the cuff is inflated so that the pressure applied by the inflated cuff is maintained near a predetermined reference pressure. A related object is to include with this tourniquet system pressure comparison means for producing an alarm if the difference between the pressure to which the cuff is inflated and the pressure applied by the inflated cuff to the limb exceeds a preassigned safety limit.

A further object of the present invention is to provide a tourniquet system comprising an inflatable occlusive cuff for encircling and applying a plurality of pressures to occlude a limb of a subject, means for controlling the pressure to which the cuff is inflated, means for sensing the plurality of pressures applied by the inflated cuff to the limb in a direction normal to the inner surface of the cuff at a plurality of predetermined locations, and including pressure comparison means for producing an alarm if the difference between the pressure to which the cuff of the tourniquet system is inflated and the pressure applied by the inflated cuff to the limb at one selected location of the plurality of predetermined locations exceeds a preassigned safety limit. A related object is to include with this tourniquet system calibration checking means for producing a calibration error signal if the difference between the pressures applied by the inflated cuff at two selected locations of the plurality of predetermined locations exceeds a preassigned difference limit.

The applicant is aware of the following United States patents which are more or less relevant to the subject matter of the applicant's invention.

| | | | | |
|---|---|---|---|---|
| 4,869,265 | 9/1989 | McEwen | 128/774 | 128/327 |
| 4,770,175 | 9/1988 | McEwen | | 128/327 |
| 4,605,010 | 8/1986 | McEwen | | 128/686 |
| 4,479,494 | 10/1984 | McEwen | 128/327 | 128/682 |
| 4,469,099 | 9/1984 | McEwen | 128/327 | 128/682 |

The applicant is also aware of the following published references which are more or less relevant to the subject matter of the applicant's invention.

J. A. McEwen and R. W. McGraw, "An adaptive tourniquet for improved safety in surgery." IEEE Transactions in Biomedical Engineering, Vol. BME-29, February 1982, pp. 122-128.

J. A. McEwen and G. F. Auchinleck, "Advances in surgical tourniquets." J. Assn. Operating Room Nurses, Vol. 36, 1982, pp. 889-896.

J. A. Shaw and D. G. Murray, "The relationship between tourniquet pressure and underlying soft-tissue pressure in the thigh." The Journal of Bone and Joint Surgery, Vol. 64-A, 1982, pp. 1148-1152.

A. C. McLaren and C. H. Rorabeck, "The pressure distribution under tourniquets." The Journal of Bone and Joint Surgery, Vol. 67-A, 1985, pp. 433-438.

R. J. Newman and A. Muirhead, "A safe and effective low pressure tourniquet." Journal of Bone and Joint Surgery, Vol. 68-B, 1986, pp. 625-628.

J. A. Shaw, W. W. Demuth, and A. W. Gillespy, "Guidelines for the use of digital tourniquets based on physiological pressure measurements." The Journal of Bone and Joint Surgery, Vol. 67-A, 1985, pp. 1086-1090.

S. E. Grice et al., "Intravenous regional anesthesia: Evaluation and prevention of leakage under the tourniquet." Anesthesiology, Vol. 65, pp. 316-320, 1986.

SUMMARY OF THE INVENTION

The invention is directed toward a tourniquet system comprising: an inflatable occlusive band for encircling a limb of a subject and for inflating to apply pressure to the encircled limb to occlude blood flow into the limb distal to the band wherein an inner surface of the band faces the limb; inflation pressure control means for controlling the pressure to which the occlusive band is inflated and for producing an inflation pressure signal representative of the pressure to which the band is inflated; and applied pressure sensing means located at a predetermined location fixed relative to the band for producing an applied pressure signal representative of the pressure applied by the inflated band to the limb in a direction normal to inner surface of the band at the predetermined location.

The invention is also directed toward a tourniquet system comprising: an inflatable occlusive band for encircling a limb of a subject and for inflating to apply pressure to the encircled limb to occlude blood flow into the limb distal to the band, wherein an inner surface of the band faces the limb; inflation pressure regulation means responsive to a variable inflation pressure regulation signal for regulating the pressure to which the occlusive band is inflated and for producing an inflation pressure signal representative of the pressure to which the band is inflated; applied pressure sensing means located at a predetermined location fixed relative to the band for producing an applied pressure signal representative of the pressure applied by the inflated band to the limb in a direction normal to inner surface of the band at the predetermined location; and pressure-regulating means responsive to the applied pressure signal for producing an inflation pressure regulation signal to maintain the pressure applied by the inflated band to the limb at the predetermined location near a predetermined reference pressure.

The tourniquet system may include pressure comparison means for comparing the difference between the pressures represented by the inflation pressure signal and the applied pressure signal and for and generating an alarm signal if the difference exceeds a preassigned limit.

The invention is further directed

BRIEF DESCRIPTION OF THE DRAWINGS

A specific embodiment of this invention has been chosen for purposes of illustration and description wherein.

DESCRIPTION OF THE SPECIFIC EMBODIMENT

The specific embodiment illustrated is not intended to be exhaustive or to limit the invention to the precise form disclosed. It is chosen and described in order to explain the principles o the invention and its application and practical use, and thereby enable others skilled in the art to utilize the invention.

Figure 2:
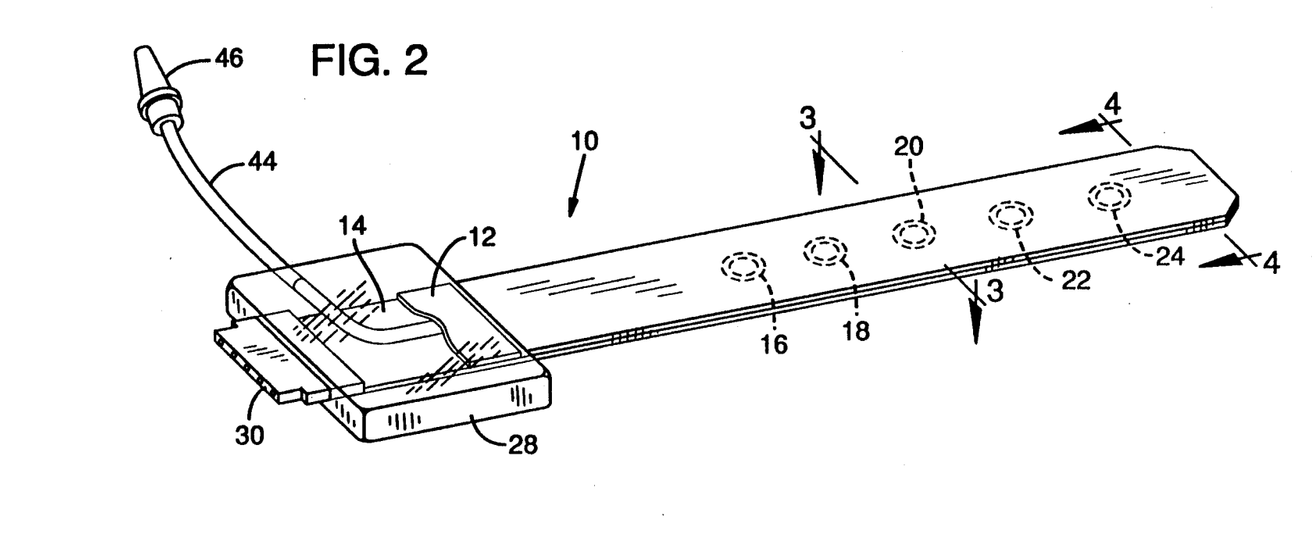
FIG. 2 is a perspective view of the transducer of FIG. 1.

The biomedical pressure transducer 10 portion of the tourniquet of this invention, as can be seen in FIG. 2, includes upper contact support layer 12 and lower contact support layer 14 which have a similar, generally rectangular shape and which are made of flexible, inextensible transparent polyester known as Mylar (DuPont trademark) that is approximately 5 mils thick.

Figure 3:
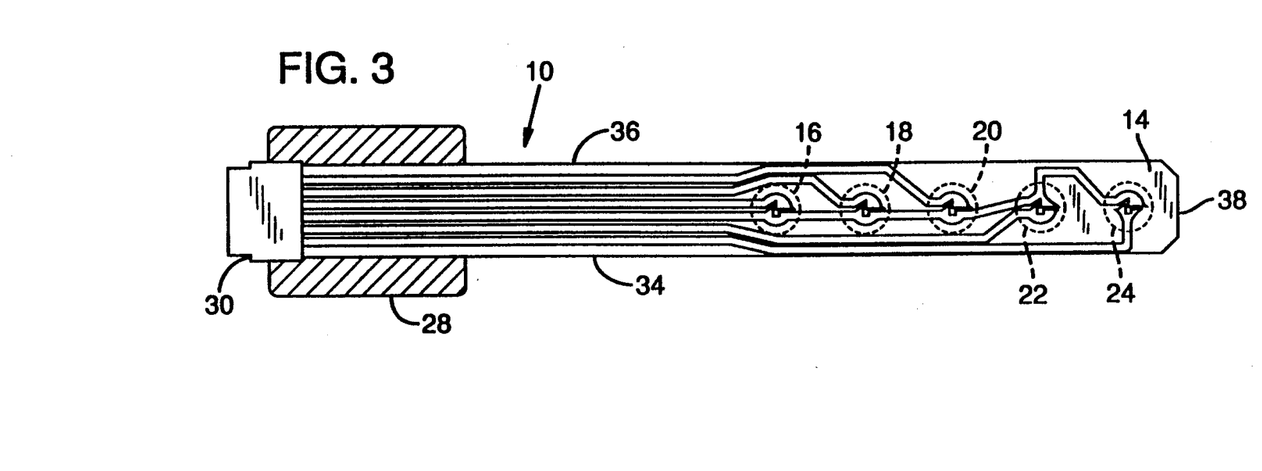
FIG. 3 is a sectional view taken along line 3—3 of FIG. 2.
Figure 4A:
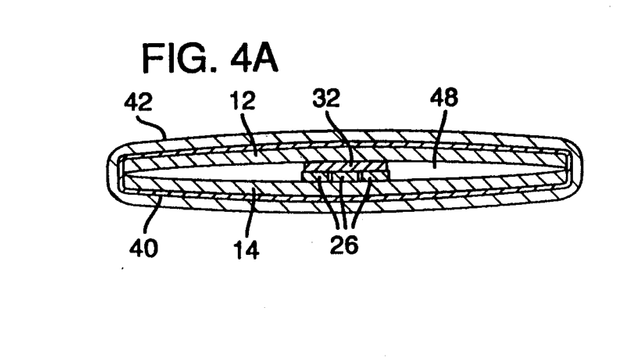
FIGS. 4A and 4B are sectional views taken along line 4—4 of FIG. 2 while the transducer is not pressurized, and while the transducer is pressurized, respectively.

FIG. 3 shows lower contact support layer 14 which has five circular switch contact areas 16, 18, 20, 22 and 24. In each switch contact area on lower contact support layer 14 are adjacent switch contacts 26 formed of a pattern of conductive silver ink (Electrodag 415SS, manufactured by Acheson Colloids, Port Huron, Mich.) having a thickness of approximately 0.4 mils and connected to leads of similar thickness formed of conductive silver ink which go through connecting block 28 to electrical connector 30. On upper contact support layer 12 directly over each of switch contact areas 16, 18, 20, 22 and 24 of lower contact support layer 14 is an upper switch contact 32 formed of a pattern of conductive silver ink having a thickness of about 0.4 mils and designed to short and form an electrical connection between adjacent switch contacts 26 on lower contact support layer 14 when the two layers are pressed together, as shown in FIG. 4A. Thus adjacent switch contacts 26 at each of the five switch contact areas 16 to 24 on lower contact support layer 14, together with the shorting upper switch contact 32 on upper contact support layer 12, form five switches located within switch contact areas 16, 18, 20, 22 and 24 near the longitudinal axis of layers 12 and 14. The five switches formed in this manner are normally closed, i.e. upper switch contact 32 is touching and shorting electrically adjacent switch contacts 26, when the upper and lower contact support layers 12 and 14 are pressed together. For the specific embodiment, upper contact support layer 12, lower contact support layer 14 and electrical connector 30 were conveniently obtained by disassembling and modifying components of a commercially available membrane switch (Brady Xymox 1×5 Membrane Switch Unit manufactured by W. H. Brady Co., Milwaukee, Wis.).

Upper and lower contact support layers 12 and 14 were sealed together along edges 34 and 36 from approximately 1 cm below electrical connector 30 to distal end 38 by first wrapping flexible, transparent adhesive tape 40 (Highland Type "371" Tape manufactured by the 3M Company, St. Paul, Minn.) around the outer surfaces of upper and lower contact support layers 12 and 14 as shown in FIG. 4A. Care was taken to seal tape 40 thoroughly to itself at distal end 38, and to assure that the entire outer surfaces of upper and lower contact support layers 12 and 14 adhered firmly to tape 40. The taped portion of layers 12 and 14 was then repeatedly dipped in a rubber coating liquid (Plastic Dip Flexible Air Dry Rubber Coating manufactured by PDI Inc., St. Paul, Minn.) which dried in air to form a thin, flexible, transparent sheath 42 which was fluid-tight and which enabled the taped and sheathed portion of transducer 10 to withstand repeated pressurization to more tan 600 mmHg without leaking or rupturing.

Figure 4B:
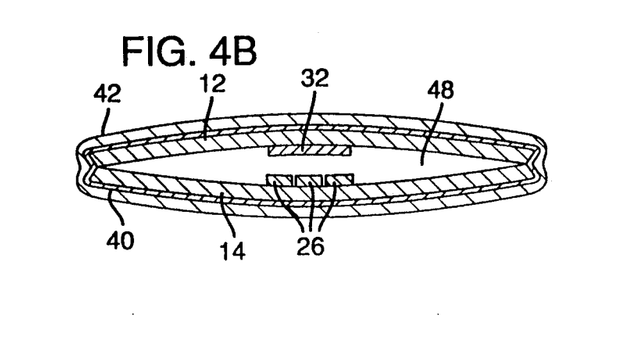

After sheath 42 was applied, the sheathed layers were positioned in relation to connecting block 28 as shown in FIG. 2. A short length of clear vinyl tubing 44 with male Luer-lock fitting 46 attached at one end was inserted through a side of connecting block 28 and then between upper and lower contact support layers 12 and 14, as shown in FIG. 2. After tubing 44 was inserted, connecting block 28 was filled with a clear epoxy resin which, when it cured, formed a strong, fluid-tight seal at the proximal end of transducer 10, thus establishing a pressurizable chamber 48 shown in FIGS. 4A and 4B. Pressurizable chamber 48 extends along substantially all of the length of sheathed contact support layers 12 and 14 and surrounds all switch contact areas 16 to 24 due to the non-zero thickness of the switch contacts and leads, as shown in FIG. 4A, and can be pressurized via the conduit means comprised of tubing 44 and Luer-lock fitting 46.

Figure 1:
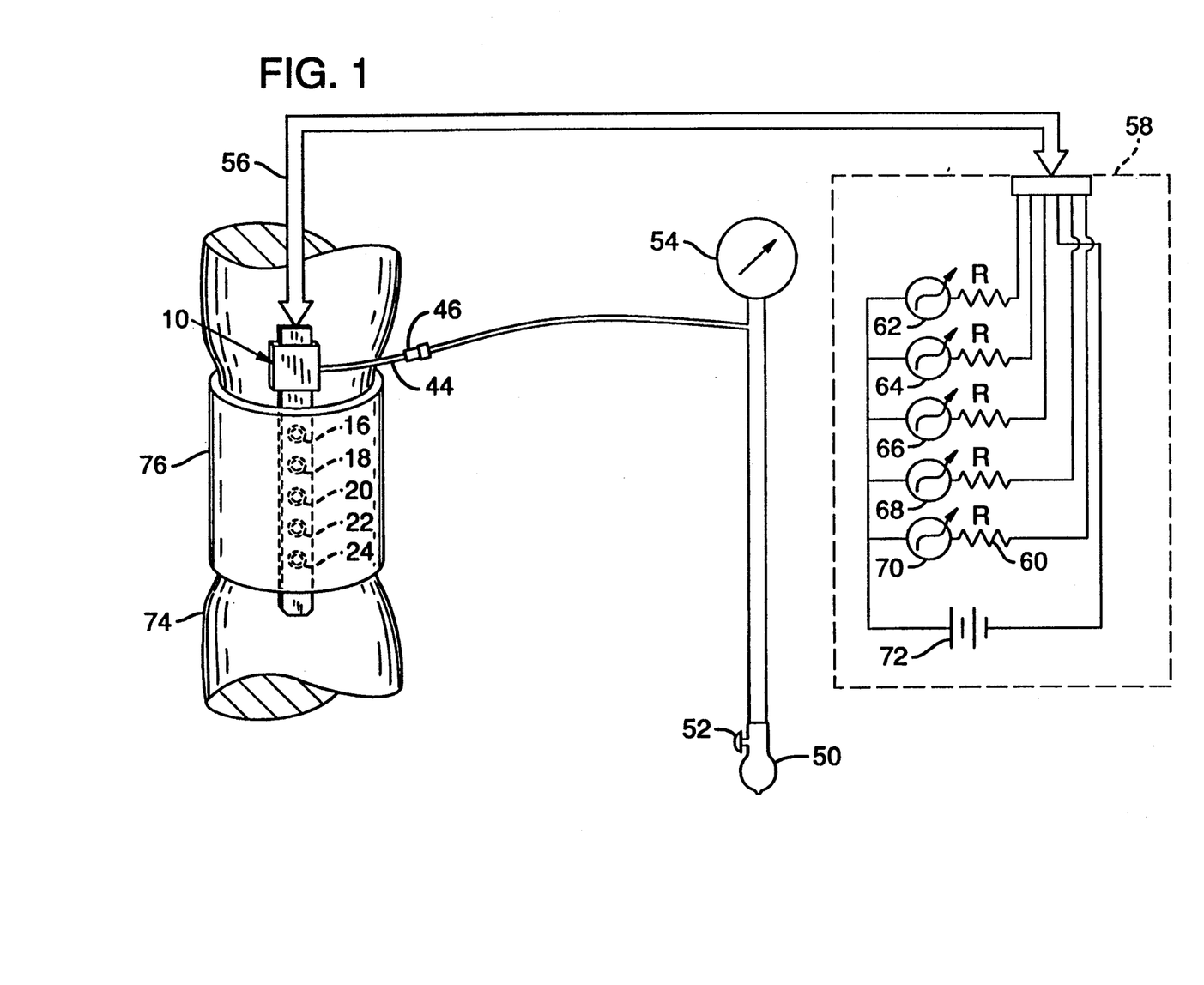
FIG. 1 is a schematic diagram depicting the biomedical pressure transducer portion of the tourniquet of this invention.

As shown in FIG. 1, in order to use transducer 10, fitting 46 is first coupled to pressurizing means 50, depressurizing means 52, and pressure-indicating means 54. In the specific embodiment, pressurizing means 50 was a hand bulb from an aneroid sphygmomanometer set, depressurizing means 52 was a manual bleed valve attached to the hand bulb, and pressure-indicating means 54 was an aneroid pressure gage. Although pressurized air is described in the specific embodiment, any pressurized fluid that is non-conductive electrically and non-reactive chemically may be employed. Transducer 10 is connected via electrical cable 56 to electrical circuitry 58, as shown in FIG. 1. Electrical circuitry 58, which includes five similar current-limiting resistors 60, five light-emitting diodes 62, 64, 66, 68 and 70, and battery 72, connects the switch contacts in each of the five switch contact areas 16 through 24 to a corresponding light-emitting diode so that light is emitted when the corresponding switch contacts are touching, i.e. when the corresponding switch is in its normally closed state.

In the simplest typical clinical application illustrated in FIG. 1, transducer 10 is attached to the inner surface of occlusive band 76 which encircles and applies pressure to limb 74. Transducer 10 is designed to be sufficiently thin, narrow and flexible so that it does not displace substantially the tissue of limb 74 from its normal location in relation to occlusive band 76, and is designed to be sufficiently long to extend above and below the edges of occlusive band 76 and to have switch contact areas 16, 18, 20, 22, and 24 positioned at proximal, mid-proximal, middle, mid-distal, and distal locations, respectively, in relation to occlusive band 76. While the pressurizable chamber 48 of transducer 10 is not pressurized, all switch contacts are touching i.e. all switches are in their normally closed state, and all light-emitting diodes 62 to 70 emit light. Pressurizable chamber 48 of transducer 10 is then gradually pressurized by an operator activating pressurizing means 50, who observes the status of light-emitting diodes 62 through 70 and at the same time observes the pressure indicated by pressure-indicating means 54. The lowest pressure at which each light-emitting diode stops emitting light is recorded: each pressure thus recorded is an estimate of the pressure applied by occlusive band 76 in a normal direction onto the surface of limb 74 beneath the corresponding switch contact area. Once pressurizable chamber 48 of transducer 10 has been pressurized sufficiently to extinguish all light-emitting diodes, the operator may use depressurizing means 52 to gradually depressurize chamber 48 of transducer 10 and record the highest pressure at which each of the light-emitting diodes begins emitting light, thus providing a second estimate of the pressure applied in a normal direction beneath the corresponding switch contact area and also providing (by comparison with the corresponding estimate obtained previously while pressure was increasing) an estimate of any inherent hysteresis that may exist in transducer 10 and in the other elements of the pressure estimation system. The set of pressure estimates obtained by manually pressurizing and depressurizing pressurizable chamber 48 of transducer 10 as described above is of intrinsic significance in many clinical applications.

Figure 5:
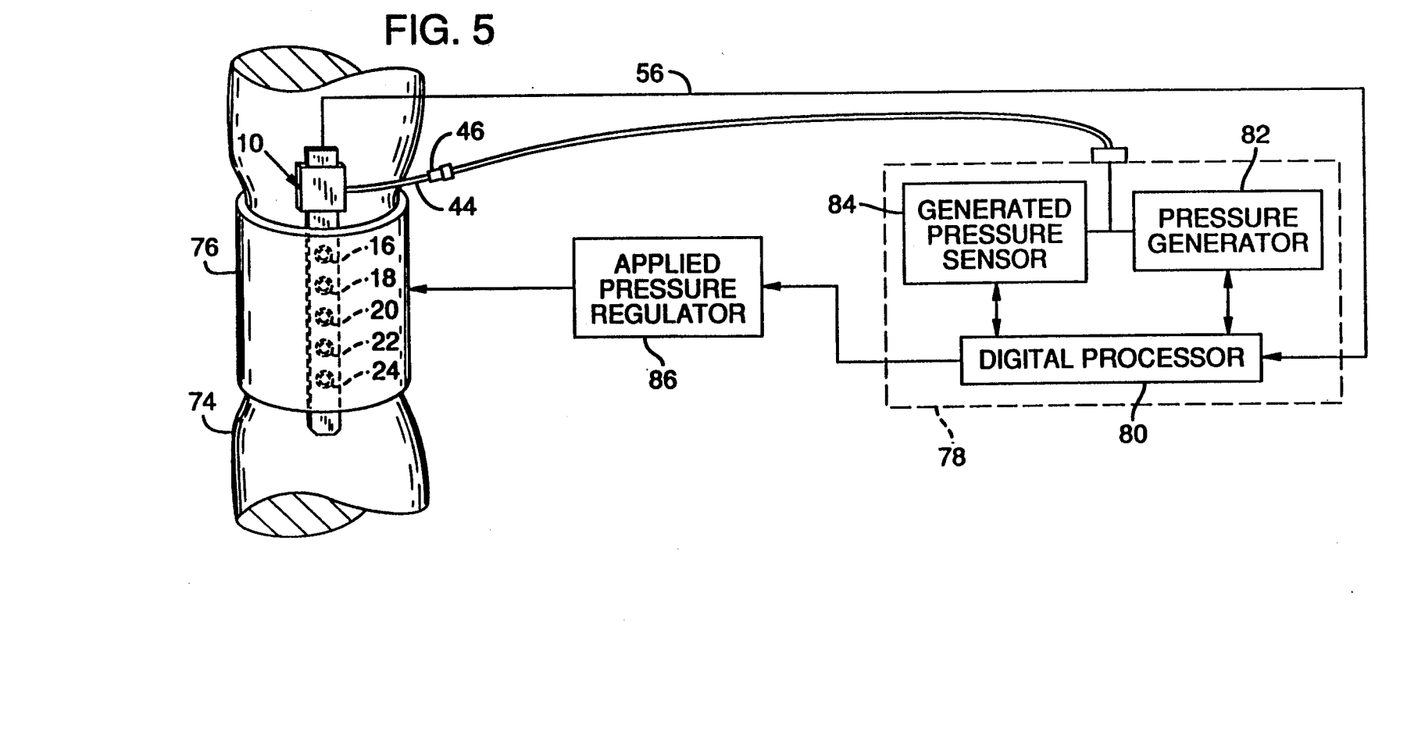
FIG. 5 is a block diagram of a tourniquet for regulating pressure applied to a limb, showing the transducer connected to electrical circuitry and apparatus for controlling the pressure applied by the occlusive band of the invention to the limb near a predetermined location relative to the band.

For more complex clinical applications where repetitive pressure estimates are required by a clinical operator, or where it is desired by the operator to automatically maintain the pressure applied to the surface of tissue beneath a selected switch contact area near a predetermined reference pressure, transducer 10 is attached to automated transducer controller 78 as shown in FIG. 5. Automated transducer controller 78 includes digital processor 80 for selectably pressurizing and depressurizing pressurizable chamber 48 of transducer 10 by controlling pressure generator 82, comprised of an electric pump and electrical pressure-relief valve. Digital processor 80 estimates the pressures applied to the surface of tissue beneath switch contact areas by reading the level of the signal produced by generated pressure sensor 84 as the switches at switch contact areas 16 to 24, which are monitored via electrical cable 56, change states during predetermined pressurization and depressurization cycles. Digital processor 80 produces an output signal representative of the pressures applied at the switch contact areas for controlling applied pressure regulator 86 in order to maintain the pressure applied to an area of the surface of limb 74 beneath a selected switch contact area near a predetermined reference pressure. This pressure regulation can be conveniently achieved in practice by, for example, interfacing the output signal of digital processor 80 to an automated tourniquet system such as one of the ATS 1500 or ATS 500 automatic tourniquet systems manufactured by Aspen Laboratories of Englewood, Colo., which then functions as applied pressure regulator 86.

An evaluation of the accuracy and hysteresis of the occlusive band 76 with transducer 10 attached may be performed by an operator when desired by placing occlusive band 76 with transducer 10 attached onto a flat surface, applying a series of known pressures to the upper surface of occlusive band 76 over transducer 10, pressurizing and depressurizing pressurizable chamber 48 of transducer 10, recording the pressures at which the switches change state, and comparing the recorded pressures to the known pressures.

Figure 6:
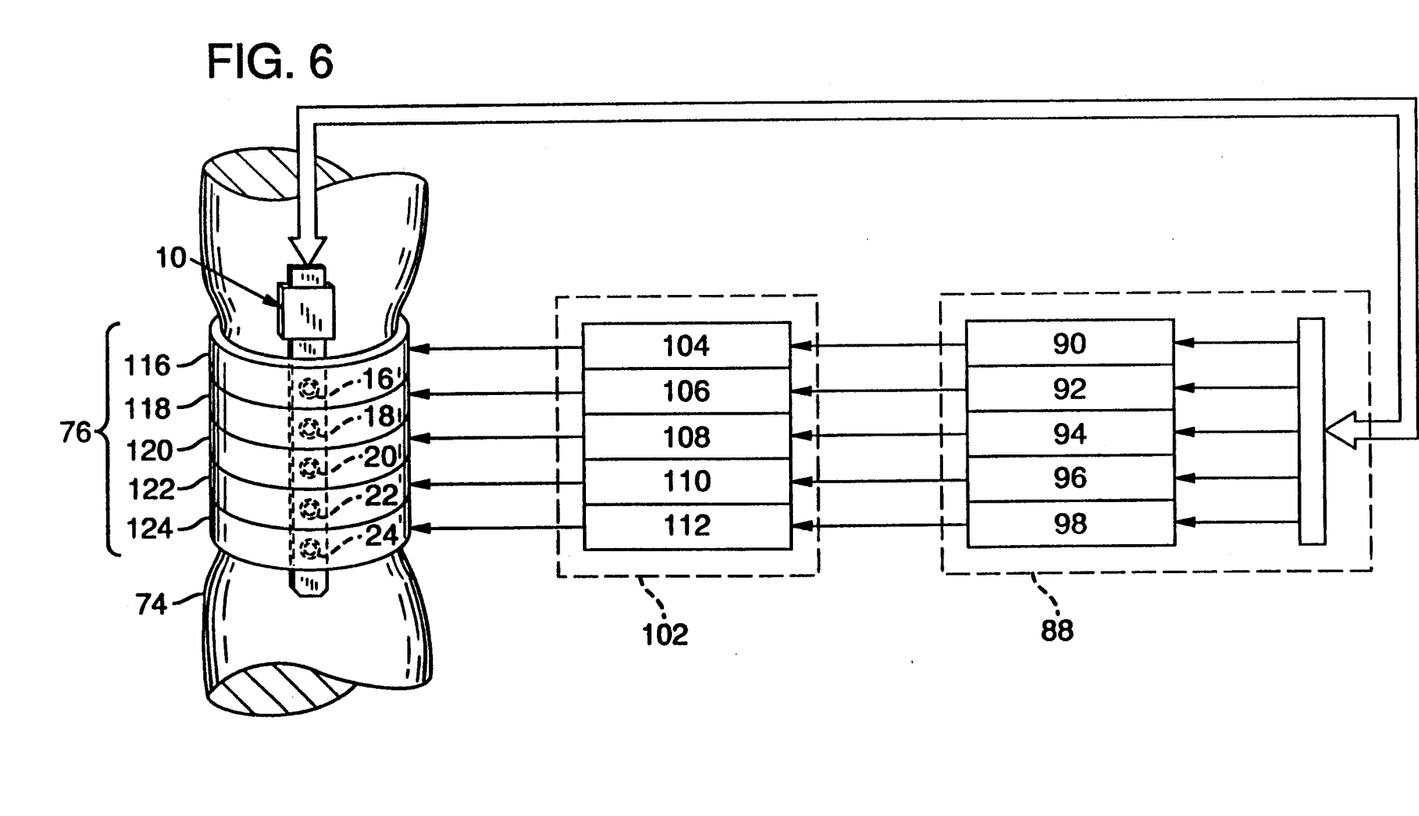
FIG. 6 is a block diagram of a tourniquet for regulating more than one pressure applied to a limb, showing an occlusive band having five separately controllable segments with the transducer connected to electrical circuitry and apparatus for separately regulating the pressure applied by each of the five segments of the occlusive band to the limb near six predetermined locations relative to the band.

FIG. 6 shows a tourniquet for separately and simultaneously regulating multiple pressures actually applied to a limb. Occlusive band 76 shown in FIG. 6 is comprised of five separately controllable segments 116, 188, 120, 122 and 124 located above switch contact areas 16, 18, 20, 22 and 24 respectively. Transducer interface 88 shown in FIG. 6 is connected to transducer 10 and is comprised of five elements 90, 92, 94, 96, 98 and 100 which produce signals representative of the pressures applied by occlusive band segments 116, 188, 120, 122 and 124 to the limit near switch contact areas 16, 18, 20, 22 and 24 respectively. Pressure controller 102 receives the five signals from transducer interface 88 and maintains the pressures applied to the surface of limb 74 beneath each of the five switch contact areas 16, 18, 20, 22 and 24 near five predetermined reference pressures.

Figure 7:
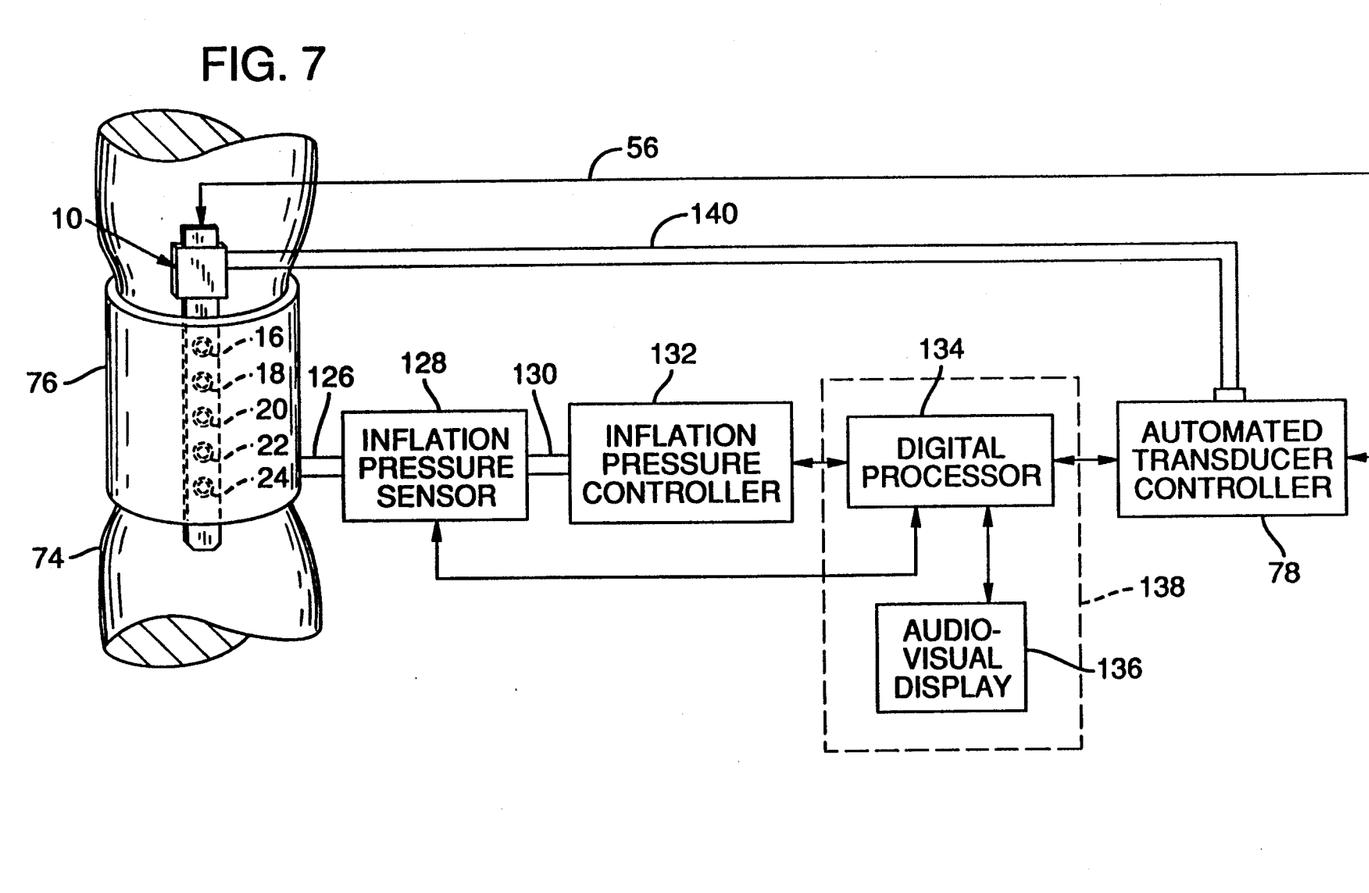
FIG. 7 is a block diagram of a tourniquet for regulating pressure applied to a limb, showing the transducer connected to apparatus for controlling the pressure applied by inflatable occlusive band of the invention to the limb near a predetermined location relative to the band, and for comparing the pressure in the inflatable occlusive band to the pressure applied by the band to the limb near a predetermined location relative to the band.

For clinical applications in which improved safety and reliability are desired, the tourniquet system of FIG. 7 provides continuous monitoring of applied pressures for generating an alarm signal in response to misapplication of occlusive band 76, calibration error associated with transducer 10, or failure of inflation pressure sensor 128. Occlusive band 76, which encircles and occludes blood flow into limb 74, is inflatable with pressurized air supplied by inflation pressure controller 132 through tubing 126, inflation pressure sensor 128, and tubing 130. Inflation pressure controller 132 may be a conventional pressure regulator for pneumatic tourniquets such as one of the ATS 1500 or ATS 500 automated tourniquet systems manufactured by Aspen Laboratories of Englewood, Colo. Biomedical pressure transducer 10 located on limb 74 at a predetermined location fixed relative to band 76 is connected through electrical cable 56 and tubing 140 to transducer controller 78, which selectably pressurizes and depressurizes chamber 48 of transducer 10 as described previously to obtain an applied pressure signal representative of the pressure applied by band 76 to limb 74 in a direction normal to the inner surface of band 76. Inflation pressure sensor 128 (Spectramed 072911-000-583, Spectramed Inc., Oxnard, Calif.) produces an inflation pressure signal representative of the pressure to which occlusive band 76 is inflated. The applied pressure signal from controller 78 and the inflation pressure signal from sensor 128 are monitored by integrated digital processor 134 (Intel 80C196, Intel Corp., Santa Clara, Calif.) of signal analyzer 138. Processor 134, which incorporates on-chip analog-to digital converter, random access memory, read-only memory, and digital input/output ports, communicates with audio-visual display 136 to provide an operator interface. In practise, display 136 may be assembled from an alphanumeric liquid crystal display (Hitachi LM040, Hitachi America Ltd., San Jose, Calif.) and a piezoelectric buzzer (Murata Erie PKB4A0, Murata Erie Inc., Smyrna, Ga.).

In operation, the user inflates band 76 via controller 132 to an inflation pressure thought to be sufficient to occlude limb 74. Processor 134 obtains the applied pressure at the predetermined location of contact 20 of transducer 10 by monitoring the applied pressure signal from controller 78. Processor 134 also monitors the inflation pressure signal from sensor 128 and compares this with the applied pressure signal. If the difference between the applied pressure signal and the inflation pressure signal exceeds a preassigned limit of +/−20 mmHg, processor 134 generates an alarm signal to the user by means of an alarm tone and simultaneous text message on audio-visual display 136.

The tourniquet system of FIG. 7 includes provision for regulation of the pressure applied by band 76 to limb 74 at a predetermined location fixed relative to band 76. As shown in FIG. 7, inflation pressure controller 132 is responsive to a variable inflation pressure regulation signal from processor 134 for regulating the pressure to which band 76 is inflated. In practise, this is accomplished through minor software modification and hardware addition to the Aspen Labs ATS 1500 or ATS 500 which is represented in FIG. 7 by controller 132. In operation, processor 134 monitors the applied pressure signal from controller 78 and communicates an inflation pressure regulation signal to controller 132. Processor 134 thereby maintains the pressure applied by band 76 to limb 74 at the predetermined location of contact 20 of transducer 10 near a predetermined reference pressure. While acting to regulate the applied pressure, processor 134 also monitors the inflation pressure signal from sensor 128 and compares this with the applied pressure signal from controller 78. If the difference between the applied pressure signal and the inflation pressure signal exceeds the preassigned limit of +/−20 mmHg, processor 134 generates an alarm signal to the user by means of an alarm tone and simultaneous text message on audio-visual display 136. In addition to these regulation and comparison functions, processor 134 communicates the applied pressure signal from controller 78 to display 136 to produce an indication of an actual pressure applied to the limb beneath transducer 10.

For purposes of calibration checking and pressure comparison, processor 143 also monitors the five applied pressure signals from controller 78 representative of the plurality of pressures applied by inflated band 76 to limb 74 in a direction normal to the inner surface of band 76 at the predetermined locations of contacts 16, 18, 20, 22 and 24 of transducer 10. Processor 134 compares the difference between the selected applied pressure signals derived by controller 78 from contacts 16 and 18 of transducer 10, and if this difference exceeds the preassigned difference limit of +/−20 mmHg, processor 134 generates a calibration error signal to the user by means of display 136. Processor 134 cyclically repeats this calibration check for contact pairs 18 and 20, 20 and 22, 22 and 24, 24 and 16, and 16 and 18 and generates the calibration error signal if any difference of the selected applied pressure signals exceeds the preassigned difference limit. While sampling each of the five applied pressure signals from controller 78 to perform the calibration check, processor 134 selects the largest of the five signals. Processor 134 compares the largest selected applied pressure signal to the inflation pressure signal from sensor 128 and generates an alarm signal to the user by means of display 136 if the difference of these signals exceeds the preassigned safety limit of +/−20 mmHg. While executing these calibration checking and pressure comparison functions, processor 134 communicates the largest selected applied pressure signal from controller 78 to display 136.

As will be apparent to those skilled in the art, in the light of the foregoing disclosure many alterations and modifications are possible in the practice of this invention without departing from the scope or spirit thereof. For example, a smaller or larger number of switch contact areas could be included, and the size, spacing, and patterns of the switch contact areas could be modified to estimate pressures near various numbers of predetermined locations on pneumatic and non-pneumatic cuffs having a wide variety of designs and physical characteristics, as could the physical dimensions and type of material used to form the upper and lower switch contact support areas. In addition, a number of other transducers other than the one disclosed may be substituted or adapted to sense single or multiple pressures applied to the limb. For example, a transducer for sensing pressures applied by a cuff to a limb at a single or number of predetermined locations could be fabricated from one or more ultrathin strain gauges which are presently used to sense air pressures on surfaces for aerospace applications, or from one or more piezoresistive transducers based on silicon microstructure technology which are presently used in a variety of automotive, robotic, and medical applications to sense gas and fluid pressures.

I claim:
1. A tourniquet system comprising:
   an inflatable occlusive band for encircling a limb of a subject and for inflating to apply pressure to the encircled limb to occlude blood flow into the limb distal to the band wherein an inner surface of the band faces the limb;
   inflation pressure control means for controlling the pressure to which the occlusive band is inflated and for producing an inflation pressure signal representative of the pressure to which the band is inflated; and
   applied pressure sensing means located at a predetermined location fixed relative to the band for producing an applied pressure signal representative of the pressure applied by the inflated band to the limb in a direction normal to inner surface of the band at the predetermined location.

2. A tourniquet as described in claim 1 and including pressure comparison means for comparing the difference between the pressures represented by the inflation pressure signal and the applied pressure signal and for generating an alarm signal if the difference exceeds a preassigned limit.

3. A tourniquet system as described in claim 1 wherein the inflatable occlusive band occludes blood flow into the limb distal to the band for the duration of a surgical procedure.

4. A tourniquet system comprising:
an inflatable occlusive band for encircling a limb of a subject and for inflating to apply pressure to the encircled limb to occlude blood flow into the limb distal to the band, wherein an inner surface of the band faces the limb;
inflation pressure regulation means responsive to a variable inflation pressure regulation signal for regulating the pressure to which the occlusive band is inflated and for producing an inflation pressure signal representative of the pressure to which the band is inflated;
applied pressure sensing means located at a predetermined location fixed relative to the band for producing an applied pressure signal representative of the pressure applied by the inflated band to the limb in a direction normal to inner surface of the band at the predetermined location; and
pressure-regulating means responsive to the applied pressure signal for producing an inflation pressure regulation signal to maintain the pressure applied by the inflated band to the limb at the predetermined location near a predetermined reference pressure.

5. A tourniquet system as described in claim 4 and including pressure comparison means for comparing the difference between the pressures represented by the inflation pressure signal and the applied pressure signal and for and generating an alarm signal if the difference exceeds a preassigned limit.

6. A tourniquet system as described in claim 4 wherein the inflatable occlusive band occludes blood flow into the limb distal to the band for the duration of a surgical procedure.

7. A tourniquet system as described in claim 4 wherein the applied pressure sensing means produces an indication of pressure during the period of time that blood flow into the limb distal to the band is occluded.

8. A tourniquet system comprising:
an inflatable occlusive band for encircling a limb of a subject and for inflating to apply a plurality of pressures to the encircled limb to occlude blood flow into the limb distal to the band, wherein an inner surface of the band faces the limb;
inflation pressure control means for controlling the pressure to which the occlusive band is inflated and for producing an inflation pressure signal representative of the pressure to which the band is inflated; and
applied pressure sensing means located at a plurality of predetermined locations fixed relative to the band for producing a plurality of applied pressure signals representative of the plurality of pressures applied by the inflated band to the limb in a direction normal to inner surface of the band at the predetermined locations.

9. A tourniquet system as described in claim 8 and including calibration checking means for comparing the difference between the pressures represented by two selected applied pressure signals and for generating a calibration error signal if the difference exceeds a preassigned difference limit.

10. A tourniquet system as described in claim 8 and including pressure comparison means for comparing the difference between the pressures represented by the inflation pressure signal and one selected applied pressure signal and for and generating an alarm signal if the difference exceeds a preassigned safety limit.

11. A tourniquet system as described in claim 8 wherein the inflatable occlusive band occludes blood flow into the limb distal to the band for the duration of a surgical procedure.

12. A tourniquet system as described in claim 8 wherein the applied pressure sensing means produces an indication of pressure during the period of time that blood flow into the limb distal to the and is occluded.

13. A tourniquet system comprising:
an inflatable occlusive band for encircling a limb of a subject and for inflating to apply pressure to the encircled limb to occlude blood flow into the limb distal to the band, wherein an inner surface of the band faces the limb;
inflation pressure regulation means responsive to a variable pressure regulation signal for regulating the pressure to which the occlusive band is inflated and for producing an inflation pressure signal representative of the pressure to which the band is inflated;
applied pressure sensing means located at a plurality of predetermined locations fixed relative to the band for producing a plurality of applied pressure signals representative of the plurality of pressures applied by the inflated band to the limb in a direction normal to the inner surface of the band at the predetermined locations;
pressure selection and regulating means responsive to the plurality of applied pressure signals for selecting an applied pressure signal and for producing an inflation pressure regulation signal to maintain the pressure applied by the inflated band to the limb at the predetermined location near a predetermined reference pressure.

14. A tourniquet system as described in claim 13 and including pressure comparison means for comparing the difference between the pressures represented by the inflation pressure signal and one selected applied pressure signal and for and generating an alarm signal if the difference exceeds a preassigned safety limit.

15. A tourniquet system as described in claim 13 wherein the inflatable occlusive band occludes blood flow into the limb distal to the band for the duration of a surgical procedure.

16. A tourniquet system as described in claim 13 wherein the applied pressure sensing means produces an indication of pressure during the period of time that blood flow into the limb distal to the band is occluded.

* * * * *

UNITED STATES PATENT AND TRADEMARK OFFICE
CERTIFICATE OF CORRECTION

PATENT NO. : 5,181,522
DATED : January 26, 1993
INVENTOR(S) : James A. McEwen

It is certified that error appears in the above-indentified patent and that said Letters Patent is hereby corrected as shown below:

In the Abstract:

Lines 26 "and for and" should be --and for--.

In the Specification:

Column 1, line 8, "5,048,." should be --5,048,536,--; and

Column 1, line 10, "4,869,." should be --4,869,265--.

Column 1, line 29, "representative indication" should be --representative--;

Column 4, line 65, "and for and" should be --and for--;

Column 4, line 70, the words "The invention is further directed" should be deleted;

UNITED STATES PATENT AND TRADEMARK OFFICE
CERTIFICATE OF CORRECTION

PATENT NO. : 5,181,522

DATED : January 26, 1993

INVENTOR(S) : James A. McEwen

Page 2 of 3

It is certified that error appears in the above-indentified patent and that said Letters Patent is hereby corrected as shown below:

Column 5, line 45, "principles o the" should be --principles of the--;

Column 5, line 56, "enable" should be --enables--;

Column 7, line 24, "touching i.e." should be --touching, i.e.--;

Column 8, lines 33-34, "comprised of" should be --and comprised of--;

Column 9, line 9, "practise" should be --practice--;

Column 9, line 33, "practise" should be --practice--;

Column 11, line 31, "and for and" should be --and for--;

Column 12, line 9, "and for and" should be --and for--; and

UNITED STATES PATENT AND TRADEMARK OFFICE
CERTIFICATE OF CORRECTION

PATENT NO. : James A. McEwen
DATED : January 26, 1993
INVENTOR(S) : 5,181,522

It is certified that error appears in the above-indentified patent and that said Letters Patent is hereby corrected as shown below:

Column 12, line 50, "and for and" should read--and for--.

Signed and Sealed this

Ninth Day of August, 1994

Attest:

BRUCE LEHMAN

Attesting Officer

Commissioner of Patents and Trademarks